US008147401B2

(12) United States Patent
Yamaya

(10) Patent No.: US 8,147,401 B2
(45) Date of Patent: *Apr. 3, 2012

(54) ENDOSCOPE INSERTION SUPPORT TOOL AND ENDOSCOPE DEVICE

(75) Inventor: Koji Yamaya, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1060 days.

This patent is subject to a terminal disclaimer.

(21) Appl. No.: 12/066,172

(22) PCT Filed: Jun. 1, 2006

(86) PCT No.: PCT/JP2006/311019
§ 371 (c)(1),
(2), (4) Date: Mar. 7, 2008

(87) PCT Pub. No.: WO2007/039956
PCT Pub. Date: Apr. 12, 2007

(65) Prior Publication Data
US 2009/0171156 A1 Jul. 2, 2009

(30) Foreign Application Priority Data
Sep. 30, 2005 (JP) .................................. 2005-288213

(51) Int. Cl.
*A61B 1/00* (2006.01)
(52) U.S. Cl. ........ 600/115; 600/104; 600/106; 600/114; 600/116
(58) Field of Classification Search .................. 600/104, 600/106, 114–116, 121–125, 127, 153
See application file for complete search history.

(56) References Cited

U.S. PATENT DOCUMENTS

| 4,453,545 | A | * | 6/1984 | Inoue ........................ 128/207.15 |
| 5,135,001 | A | * | 8/1992 | Sinofsky et al. .............. 600/459 |
| 5,231,365 | A | * | 7/1993 | Kato .............................. 335/132 |
| 5,578,009 | A | * | 11/1996 | Kraus et al. ................. 604/95.04 |
| 6,022,340 | A | * | 2/2000 | Sepetka et al. ................ 604/500 |
| 6,277,065 | B1 | * | 8/2001 | Donofrio ....................... 600/115 |
| 6,746,441 | B1 | * | 6/2004 | Hofmann et al. ............. 604/522 |
| 6,953,431 | B2 | * | 10/2005 | Barthel ......................... 600/116 |
| 7,635,345 | B2 | * | 12/2009 | Gross et al. ................. 604/99.01 |
| 7,699,861 | B2 | * | 4/2010 | Bayer ........................... 606/159 |

(Continued)

FOREIGN PATENT DOCUMENTS

EP        0 402 467 A1        12/1990

(Continued)

*Primary Examiner* — Matthew J Kasztejna
(74) *Attorney, Agent, or Firm* — Scully, Scott, Murphy & Presser, P.C.

(57) ABSTRACT

An endoscope insertion support tool includes an advancing and retracting member that is disposed in an insertion section of an endoscope, capable of advancing and retracting in a hollow passage, a distal end portion of which communicates with the outside, and has length projected from a distal end of the insertion section, a balloon member that includes an attaching portion attachable to an outer surface side of the insertion section of the endoscope and is connected to the distal end of the advancing and retracting member and capable of projecting from the distal end of the insertion section according to an advancing and retracting movement of the advancing and retracting member, and a fluid supplying and discharging unit including a conduit that is connected to the balloon member and inflates and deflates the balloon member according to supply and discharge of a fluid to and from the balloon member.

29 Claims, 17 Drawing Sheets

U.S. PATENT DOCUMENTS 7,775,968 B2 * 8/2010 Mathis .................. 600/104
7,798,992 B2 * 9/2010 Ortiz .................. 604/95.01

FOREIGN PATENT DOCUMENTS

| JP | 59-181121 | 10/1984 |
| JP | 01-207078 | 8/1989 |
| JP | 08-299261 | 11/1996 |
| JP | 2003-135388 | 5/2003 |
| JP | 2005-230081 | 9/2005 |
| WO | WO 89/07413 | 8/1989 |

* cited by examiner

FIG.8
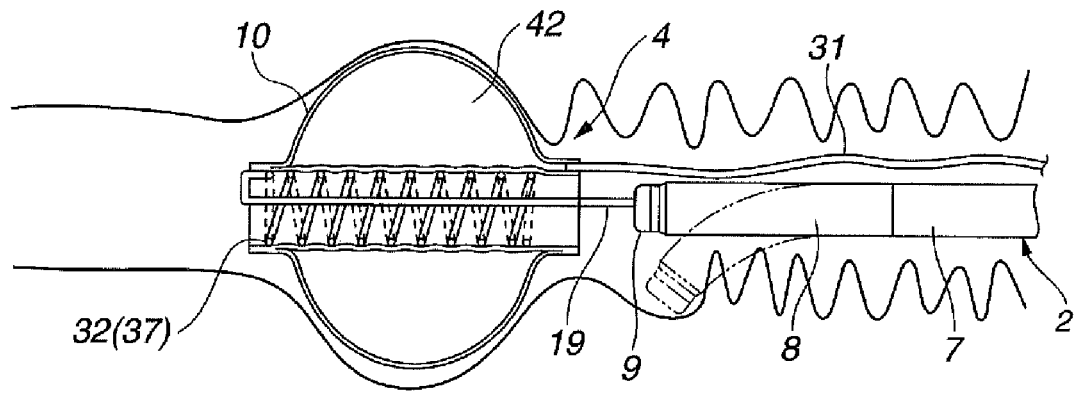
FIG. 9 (A)    FIG. 9 (B)
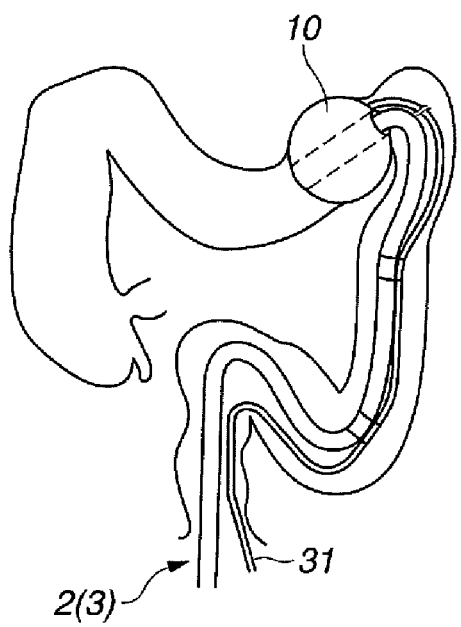
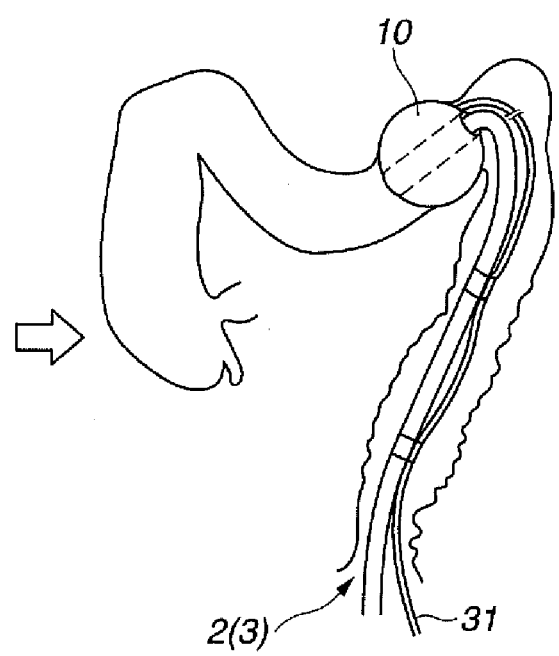

ENDOSCOPE INSERTION SUPPORT TOOL AND ENDOSCOPE DEVICE

TECHNICAL FIELD

The present invention relates to an endoscope insertion support tool and an endoscope device suitable for smoothly inserting an insertion section of an endoscope into tube cavities such as a large intestine and a small intestine, for example, per anus or per os.

BACKGROUND ART

In general, an endoscope includes an operation section that an operator grasps to perform various kinds of operation and an insertion section. The insertion section includes a flexible portion that is a slim tube extended from the operation section and has flexibility, a bending portion that is continuously provided to a distal end of the flexible portion and is bendable in a left and right or an up and down direction, and a rigid distal end portion that is continuously provided to a distal end of the bending portion. The operator inserts the insertion portion into a body cavity per anus, per os, or per naso, observes and diagnoses a predetermined region, or performs treatment or the like while observing the region.

Incidentally, to inert the insertion section of the endoscope into the body cavity, in the past, a method of pushing in the insertion portion of the endoscope by applying a force to the insertion portion from the outside of the body of a patient is adopted.

However, in such a push-in method, when the insertion portion is inserted into a large intestine or a small intestine per anus or per os, it may be difficult to smoothly perform the insertion as described below.

Intestinal tracts of the large intestine, the small intestine, and the like are small in a tube cavity inner diameter, long, and complexly wind and, moreover, are not firmly fixed, and are flexible. Therefore, even if the operator moves or compresses the insertion section of the endoscope in a moving direction by pushing in the insertion section, when the operator releases the push-in force, the insertion section is pushed back to nearly an original position by a reaction. Therefore, the insertion section does not easily advance in the moving direction and, in particular, in the depth of the intestinal tract, the insertion section is conspicuously pushed back. When the insertion section is inserted into the depth, in particular, an inspection time is long and insertion work of the insertion section is difficult.

Therefore, in order to make it possible to insert the insertion section of the endoscope into the intestinal tract without pushing in the insertion section by applying a force thereto from the outside of the body of the patient, as a first prior example, an endoscope insertion support tool is disclosed in Japanese Patent Application Laid-Open No. 59-181121.

The endoscope insertion support tool in the first prior example has a balloon that is inflated and deflated by injection and discharge of a fluid at a distal end of a slim tube having flexibility. A fluid outflow and inflow device that injects and discharges the fluid into and out of the balloon for inflation and deflation is connectable to a rear end of the tube. An operator inserts the endoscope insertion support tool into a forceps channel of an endoscope from a side close to the operator, causes the balloon to project from a distal end of the endoscope and allows the balloon to move close to and away from the distal end. The operator holds and releases the intestinal tract by inflating and deflating the balloon and inserts the endoscope into the depth.

As a second prior example, in Japanese Patent Application Laid-Open No. 8-299261, a balloon that is inflated in a radial direction of an insertion section of an endoscope is provided on an outer peripheral surface of an endoscope tube equivalent to the insertion section. The balloon is provided to be capable of advancing and retracting on the outer peripheral surface of the endoscope tube by a feed screw mechanism arranged in the endoscope tube. In the endoscope tube, a flexible air tube that supplies the air to the balloon is disposed. The balloon is inflated and deflated by an air pressure regulator.

However, in the endoscope insertion support tool in the first prior example, since the balloon has to be fully inserted through the forceps channel of the endoscope, in reality, only a small balloon can be attached. Therefore, a holding force for the intestinal tract is small when the balloon is inflated. Since the holding force is small in this way, the intestinal tract tends to shift in a state in which the intestinal tract should be held. It is extremely difficult to move the endoscope forward into the depth of the intestinal tract.

In the endoscope in the second prior example, since an advancing and retraction amount of the balloon depends on a size of an opening hole opened on the outside of the endoscope tube, a movement amount of the balloon for moving the endoscope forward is limited. Therefore, it takes time to insert the endoscope.

In the second prior example, since the balloon is provided further on a proximal end portion side than the distal end portion of the endoscope, the balloon prevents the insertion in a visual field direction. Thus, it is impossible to grasp the bent intestinal tract, remove the bend, and check a state of the intestinal tract in inserting the endoscope in the visual field direction. Since it is impossible to check the state of the intestinal tract in this way, it is difficult to smoothly insert the endoscope into the depth of the intestinal tract.

The present invention has been devised in view of the points described above and it is an object of the present invention to provide an endoscope insertion support tool and an endoscope device that can smoothly insert, in inserting an insertion section of an endoscope into a tube cavity of a large intestine, a small intestine, or the like, for example, per anus or per os, the insertion section to a depth side and can attain a reduction in an inspection time and the like.

DISCLOSURE OF INVENTION

Means for Solving the Problem

An endoscope insertion support tool according to the present invention includes an advancing and retracting member that is disposed in an insertion section of an endoscope, capable of advancing and retracting in a hollow passage, a distal end portion of which communicates with the outside, and has length projected from a distal end of the insertion section, a balloon member that includes an attaching portion attachable to an outer surface side of the insertion section of the endoscope and is connected to the distal end of the advancing and retracting member and capable of projecting from the distal end of the insertion section according to an advancing and retracting movement of the advancing and retracting member, and fluid supplying and discharging means including a conduit that is connected to the balloon member and inflates and deflates the balloon member according to supply and discharge of a fluid to and from the balloon member.

With the configuration described above, the balloon member is moved between a projection from the distal end of the insertion section and an outer surface of the insertion section by operation for advancing and retracting the advancing and retracting member. The balloon member is inflated and deflated by supply and discharge of the fluid. This makes it easy to smoothly insert the insertion section of the endoscope to a depth side in a tube cavity.

An endoscope device according to the present invention includes an endoscope including a slim insertion section that is insertable into a body cavity and is provided with an illumination window and an observation window at a distal end portion thereof, an advancing and retracting member that is disposed in the insertion section, capable of advancing and retracting in a hollow passage, a distal end portion of which communicates with the outside, and has length projected from a distal end of the insertion section, a balloon member that includes an attaching portion attachable to an outer surface side of the insertion section and is connected to the distal end of the advancing and retracting member and capable of projecting from the distal end of the insertion section according to an advancing and retracting movement of the advancing and retracting member, and a conduit that is connected to the balloon member and inflates and deflates the balloon member according to supply and discharge of a fluid to and from the balloon member.

With the configuration described above, it is easily to smoothly insert the insertion section of the endoscope to a depth side in a tube cavity.

BRIEF DESCRIPTION OF THE DRAWINGS

FIG. 8 is a diagram showing a state in which operation for pulling in the shaft is performed in the state in FIG. 7 and the intestinal tract is drawn in;

FIGS. 9A and 9B are explanatory diagrams of an action for inserting the endoscope to a depth side of a large intestine;

BEST MODE FOR CARRYING OUT THE INVENTION

Embodiments of the present invention will be hereinafter explained with reference to the drawings.

First Embodiment

A first embodiment of the present invention is explained with reference to FIGS. 1 to 10.

Figure 1:
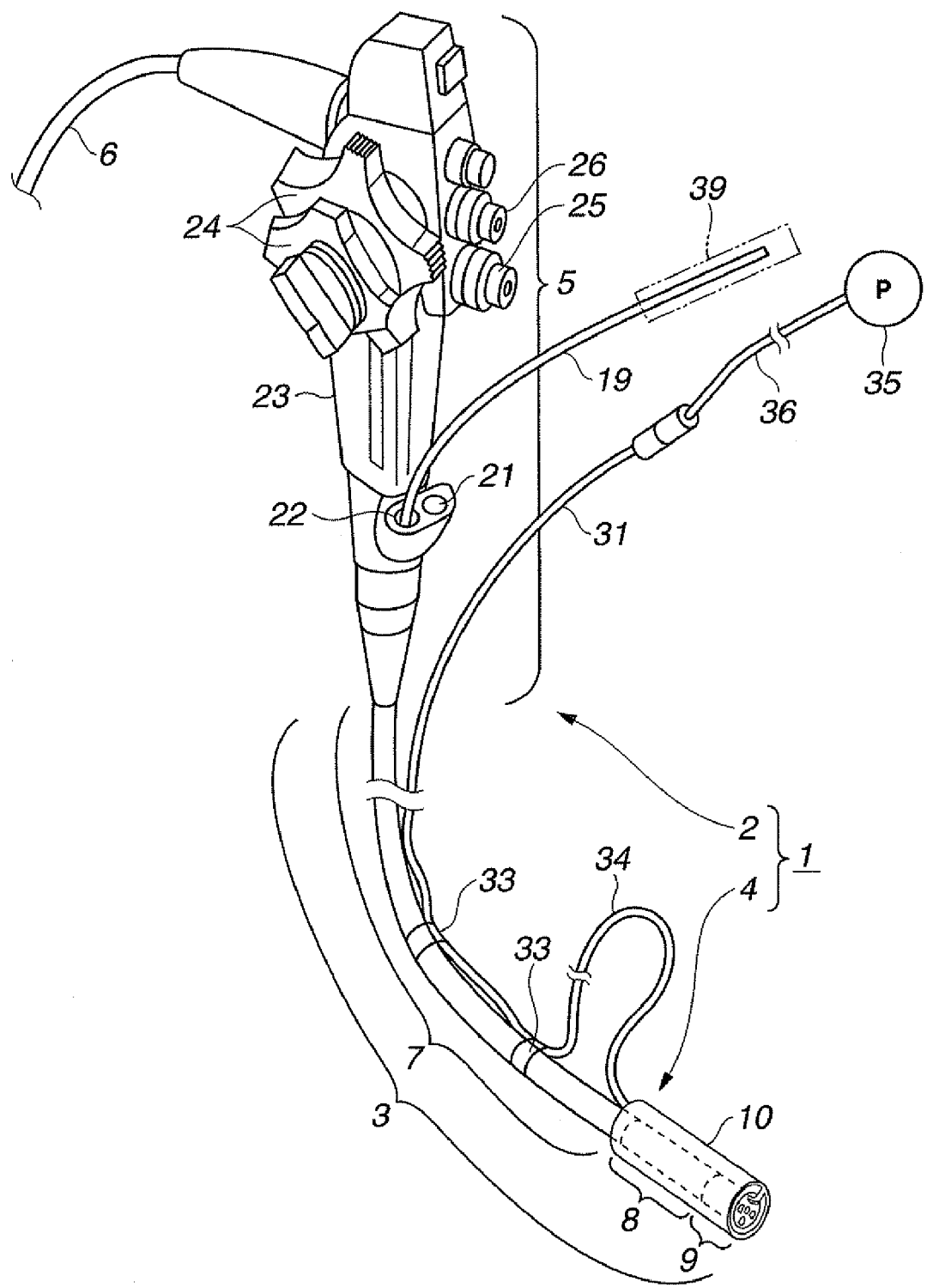
FIG. 1 is a perspective view showing an overall configuration of an endoscope device according to a first embodiment of the present invention.

As shown in FIG. 1, an endoscope device 1 according to the first embodiment of the present invention includes an endoscope 2 used for an endoscope inspection and an endoscope insertion support tool 4 that is detachably attached to a distal end side of an insertion section 3 of the endoscope 2 and supports insertion of the endoscope 2.

The endoscope 2 has a slim insertion section 3 that is inserted into a body cavity, an operation section 5 that is provided at a proximal end of the insertion section 3, and a universal cable 6 that is extended from a side of the operation section 5. A not-shown connector is provided at an end of the universal cable 6. The connector is detachably connected to a light source device and a signal processing device.

The insertion section 3 has a slim flexible tube portion 7 having flexibility, a bendable bending portion 8 that is coupled to a distal end of the flexible tube portion 7, and a rigid distal end portion 9 that is coupled to a distal end of the bending portion 8.

As shown in FIG. 1, a balloon 10 configuring the endoscope insertion support tool 4 is attached to outer peripheral surfaces of the distal end portion 9 and the bending portion 8.

Figure 2:
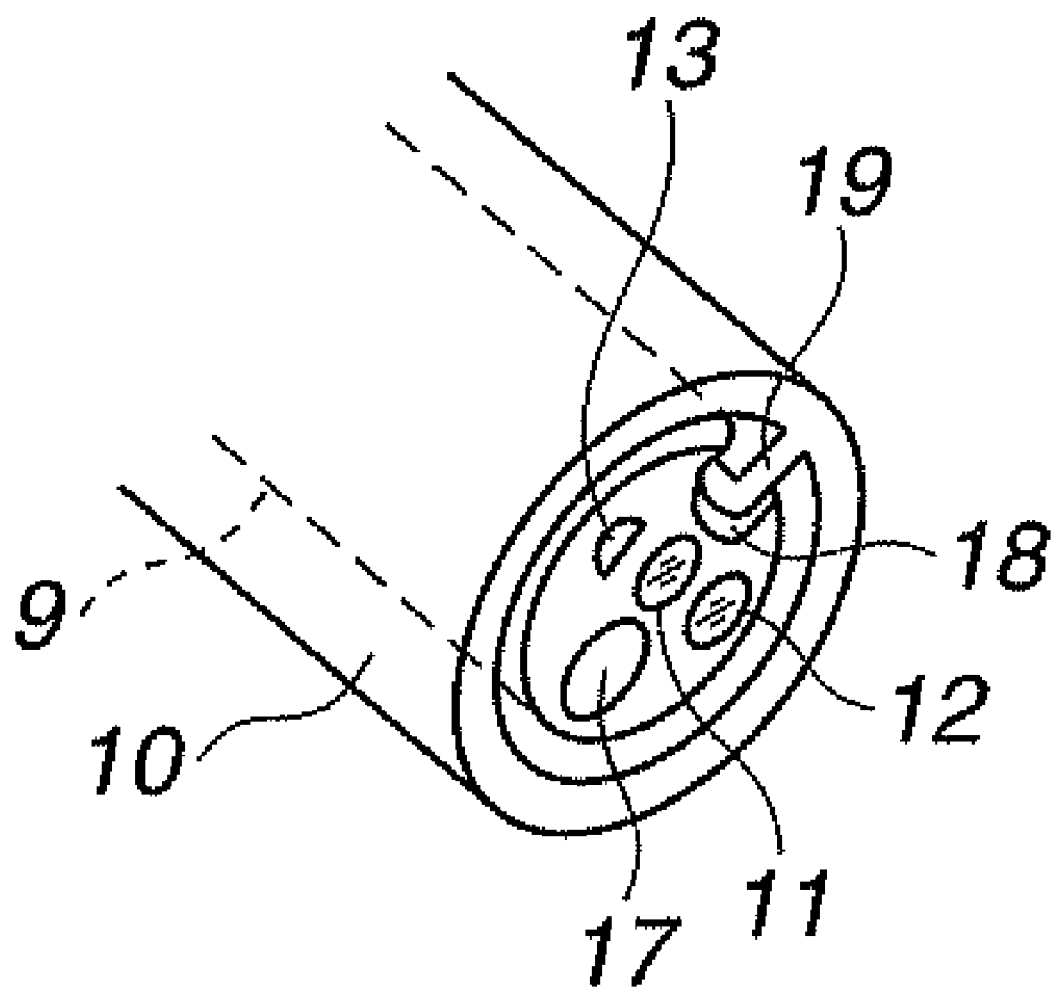
FIG. 2 is a perspective view showing a part of a distal end portion of an endoscope attached with an endoscope insertion support tool in enlargement.

In the distal end portion 9, an observation window 11 is provided, for example, near the center of a distal end surface as shown in FIG. 2 in which the distal end in FIG. 1 is enlarged. An illumination window 12 and an air-supply and water-supply nozzle 13 are provided on both sides of the observation window 11, respectively.

A light guide that transmits illumination light is inserted through on an inner side of an illumination lens attached to the illumination window 12. The light guide is inserted through the insertion section 3 and the like and detachably connected to the light source device. Illumination light generated by the light source device is transmitted by the light guide and emitted from the illumination window 12. The inside of a body cavity as a visual field range (indicated by θ in FIG. 4) of the observation window 11 is illuminated by the illumination light.

Figure 3:
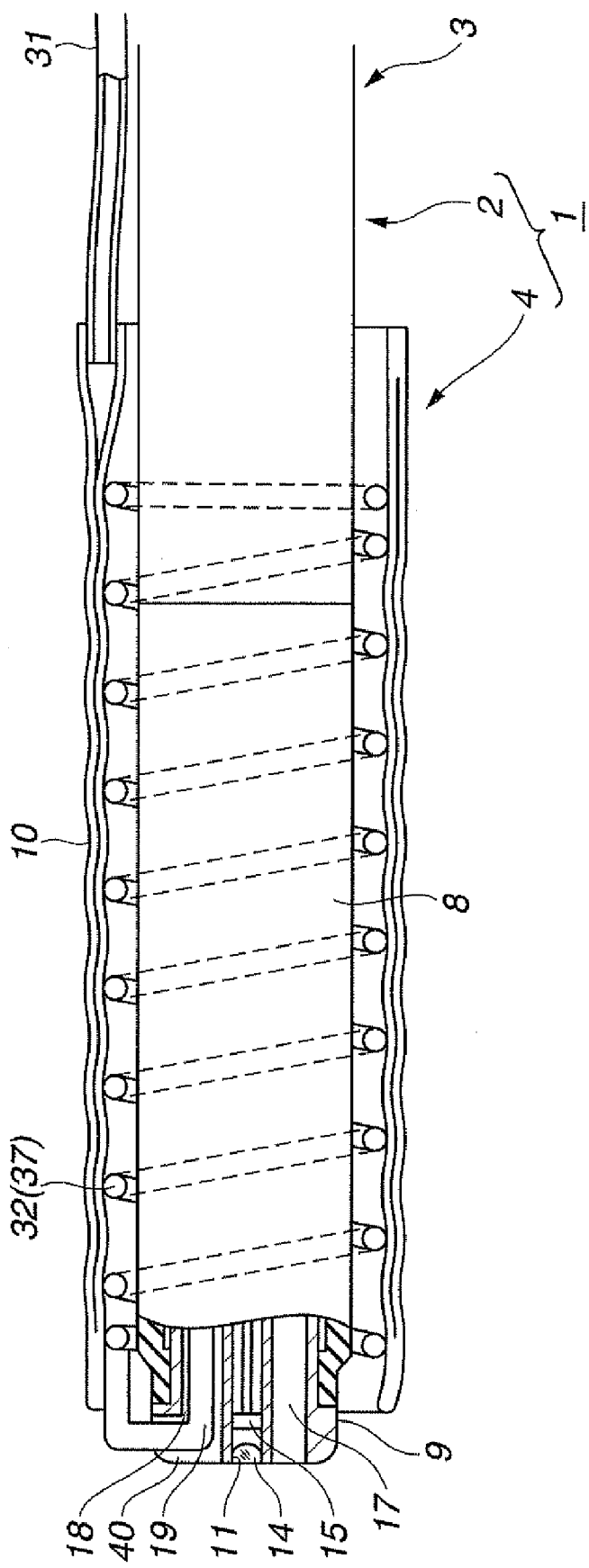
FIG. 3 is a sectional view showing a distal end side of an insertion section of the endoscope attached with the endoscope insertion support tool.

As shown in FIG. 3, an object lens 14 is attached to the observation window 11. For example, a CCD 15 is arranged as an image pickup device in an image-forming position of the object lens 14. The CCD 15 photoelectrically converts an optical image in the body cavity focused on an image pickup surface thereof.

The CCD 15 is connected to a signal cable. The signal cable is inserted through the insertion section 3 and the like and electrically connected to the signal processing device. The signal processing device applies signal processing to an image pickup signal picked up by the CCD 15, generates a video signal and outputs the video signal to a monitor, and displays an image picked up by the CCD 15 on a display surface of the monitor.

As shown in FIG. 2, opening portions at distal ends of a first channel 17 and a second channel 18 are opened on both side in a direction substantially orthogonal to a direction of the illumination window 12 and the air-supply and water-supply nozzle 13 in the observation window 11, respectively.

As also shown in FIG. 3, a shaft (a shaft body) 19 as an advancing and retracting member, which is moved to freely advance and retract in the endoscope insertion support tool 4, is inserted through the second channel 18.

The first channel 17 and the second channel 18 formed along a longitudinal direction of the insertion section 3 respectively communicate with a first channel insertion port 21 and a second channel insertion port 22 provided near a front end of the operation section 5 shown in FIG. 1.

As shown in FIG. 1, a grasping portion 23 is provided in a section close to the front end of the operation section 5. An operator can grasp the grasping portion 23 and perform, for example, operation of a bending operation knob 24 provided in the operation section 5.

In other words, the bending operation knob 24 is provided further on a rear end side than the grasping portion 23 in the operation section 5. The operator can operate to rotate the bending operation knob 24 with a finger of one hand that grasps the grasping portion 23. The operator can bend the bending portion 8 in arbitrary up and down and left and right directions according to the rotating operation.

The bending portion 8 is configured by rotatably coupling plural annular bending pieces in a longitudinal direction of the bending portion 8 to make it possible to bend the bending pieces configuring the bending portion 8 via a bending wire according to the rotating operation of the bending operation knob 24.

As shown in FIG. 1, an air-supply and water-supply button 25 and a suction button 26 that performs suction operation are provided on a surface adjacent to a surface on which the bending operation knob 24 is provided in the operation section 5. The operator can supply the air or supply water by operating the air-supply and water-supply button 25. The operator can suck a body fluid and other fluids from a distal end opening of the first channel 17 via the first channel 17 by operating the suction button 26.

The first channel 17 can be used as a conduit through which a treatment instrument is inserted and can also be used as a suction conduit for sucking the fluids. Therefore, near the front end in the operation section 5, a rear end side of the first channel 17 branches to a conduit communicating with the first channel insertion port 21 and a suction conduit extending to a rear end side of the operation section 5 (not shown).

The operator can project a distal end side of the treatment instrument inserted from a distal end opening of the distal end portion 9 via the first channel 17 inside the first channel insertion port 21 and perform biopsy and other treatments under the observation through the observation window 11 by inserting the treatment instrument from the first channel insertion port 21.

FIG. 3 shows the structure of the distal end side of the insertion section 3 in a state in which the endoscope insertion support tool 4 is attached.

The endoscope insertion support tool 4 is detachably attached to an outer peripheral surface on the distal end side of the insertion section 3. The endoscope insertion support tool 4 mainly include a balloon 10 as an inflating/deflating member (a balloon member) that inflates and deflates, a fluid tube 31 as a conduit for feeding a fluid such as the air for inflating/deflating the balloon 10, a balloon holding member 32 that holds the balloon 10, and a shaft 19 that moves the balloon 10 and the balloon holding member 32 to freely advance and retract.

The endoscope insertion support tool 4 may be a disposable product that is discarded after being used once or may be a reusable product that is reused by being cleaned, disinfected, and sterilized after use.

The balloon 10 that is inflated and deflated by the supply and discharge of a fluid is formed in a hollow bag shape with a member abundant in stretching properties, for example, latex. In a deflated state, the balloon 10 has a substantially cylindrical shape as shown in FIG. 3. An inner peripheral surface side of the cylindrical shape is held by the balloon holding member 32. The balloon 10 is detachably attached to a columnar outer peripheral surface near the distal end portion 9. The fluid tube 31 is made of, for example, a silicon tube.

As in an embodiment described later, the balloon 10 may be detachably attached to the outer peripheral surface near the distal end portion 9 of the insertion section 3 without using the balloon holding member 32. In this case, when the balloon 10 is deflated, a cylindrical and hollow inner peripheral surface may be formed to make it easy to detachably attach the balloon 10 to the outer peripheral surface near the distal end portion 9 of the insertion section 3 (a cylindrical and hollow inner peripheral surface portion may be formed thick to be prevented from being substantially changed by the supply and discharge of the fluid).

A distal end of the fluid tube 31 is coupled and fixed to a rear end side of the balloon 10 to communicate with a hollow portion therein.

For example, as shown in FIG. 1, the fluid tube 31 is fixed in plural places on an outer peripheral surface of the flexible tube portion 7 by a medical tape 33.

In this case, a sagging portion 34 is formed between a connecting portion to the balloon 10 and a fixing position by the medical tape 33 at a most distal end in the fluid tube 31. The sagging portion 34 forms a margin length that allows the balloon 10 and the balloon holding member 32 attached near the distal end portion 9 to project to the front from the distal end portion 9 by about at least 50 cm. It is possible to insert and move the endoscope 2 in the intestinal tract within a range of the margin length.

A rear end of the fluid tube 31 is detachably and hermetically connected in a connecting portion at a front end of a tube 36 connected to a balloon control pump 35 serving as fluid supplying and discharging means.

An operation of the balloon control pump 35 can be controlled by turning on and off a not-shown balloon control switch. The operator can freely supply the fluid such as the air into the balloon 10 to inflate the balloon 10 and suck and discharge the fluid to deflate the balloon 10 from the balloon control pump 35 via the fluid tube 31 by operating the balloon control switch.

The fluid such as the air may be manually supplied and discharged using a syringe or the like instead of using the balloon control pump 35.

The balloon holding member 32 is a flexible member having flexibility and includes a spring 37 made of, for example, Teflon (registered trademark) as fluorine resin. The spring 37 is formed of a spiral coil having an inner diameter size that fits in the outer peripheral surfaces of the distal end portion 9 and the bending portion 8 and detachable from the outer peripheral surfaces. The spiral coil is circular in a section thereof and has a function of an attaching portion that is detachably attached to the outer peripheral surfaces of the distal end portion 9 and the bending portion 8 on an inner surface of the spiral coil.

The balloon holding member 32 are not limited to the spring 37 in a material and the structure thereof and may be, for example, a mesh fluorine resin tube or a fluorine resin tube that is more rigid and less stretchable than the balloon 10 as an alternative member thereof as long as the member has flexibility.

The balloon 10 as a balloon member and the balloon holding member 32 detachably attached near the distal end portion 9 of the endoscope 2 have a holding structure obtained by simply spreading and placing the balloon 10 over the balloon holding member 32. However, both the members may be bonded and fixed by an adhesive or the like.

The shaft 19 as an advancing and retracting member that advances and retracts in portions of the balloon 10 and the balloon holding member 32 (hereinafter referred to as balloon peripheral portion) is a flexible member and is a bar material made of, for example, fluorine resin. The shaft 19 is not limited in a material and the structure thereof and may be, for example, a coil or the like formed using a stainless steel material as an alternative member as long as the member has flexibility.

In an example shown in FIG. 3, the shaft 19 is configured by integral molding of a material same as that of the balloon holding member 32. However, the shaft 19 may be separate from the balloon holding member 32 and fixed to the balloon holding member 32 by an adhesive or the like.

The shaft 19 is inserted through a passage formed by the second channel 18 provided in the insertion section 3 of the endoscope 2.

A rear end side of the shaft 19 is extended to the outside from the second channel insertion port 22. The operator can move the balloon peripheral portion to the front side of the distal end portion 9 and perform work for supporting insertion by performing operation for pushing out a rear end of the shaft 19 and pulling in the rear end to the side close to the operator.

The operator may connect the rear end of the shaft 19 to a driving unit 39 as indicated by an alternate long and two short dashes line in FIG. 1 and drive the driving unit 39 to electrically perform a forward movement and a backward movement of the shaft 19 according to switch operation of a not-shown foot switch or the like instead of performing operation for moving the shaft 19.

As shown in FIG. 3, a recess 40 extending to the outer peripheral surface side is formed in a distal end side opening of the second channel 18. In the state shown in FIG. 3, a return portion of the shaft 19 configuring the endoscope insertion support tool 4 is detachably fit in the recess 40.

As shown in FIG. 3, the observation window 11 and the like described above are provided on the distal end surface of the endoscope 2. Under the observation through the observation window 11, as explained below, it is possible to perform work for inserting the insertion section 3 to the depth side in the body cavity smoothly and in a short time by, for example, moving a balloon peripheral member to the front side of the distal end portion 9.

In other words, in the endoscope device 1 according to the present embodiment, the balloon peripheral portion in the endoscope insertion support tool 4 is detachable to the outer peripheral surface near the distal end portion 9 of the insertion section 3 of the endoscope 2 (in a state in which the balloon 10 is deflated) and the balloon peripheral member is movable to a front side within the visual field range of the endoscope 2 to make it easy to perform work for supporting insertion of the endoscope as explained below.

In the present embodiment, the balloon 10 is easily attached to the outer peripheral surface near the distal end portion 9 of the insertion section 3 starting from the distal end side thereof to make it possible to attach the balloon 10 having a relatively large size. Consequently, when the balloon 10 is inflated by the fluid, the endoscope insertion support tool 4 holds the intestinal tract with a large holding force to make it possible to surely move the endoscope 2 forward.

Actions in inserting the endoscope 2 according to the present embodiment having the configuration described above into the body cavity and performing an endoscope inspection are explained below.

Before performing the endoscope inspection, as shown in FIG. 3, the operator inserts the shaft 19 from the distal end side opening of the second channel 18 and attaches the endoscope insertion support tool 4 near the outer peripheral surface of the distal end portion 9 of the endoscope 2 (in FIG. 3, near the outer peripheral surfaces of the distal end portion 9 and the bending portion 8).

The rear end side of the shaft 19 is lead out to the outside from the first channel insertion port 22 as shown in FIG. 1. The operator can grasp the shaft 19 and perform operation for advancing and retracting the shaft 19.

When the inside of the body cavity is inspected, as shown in FIG. 3, the endoscope 2 is inserted into the body cavity starting from the distal end side thereof in a state in which the balloon 10 is deflated. However, thereafter, the distal end of the endoscope 2 does not easily advance in the body cavity. An operation method according to the present embodiment in this case is explained with reference to FIGS. 4 to 8.

Figure 4:
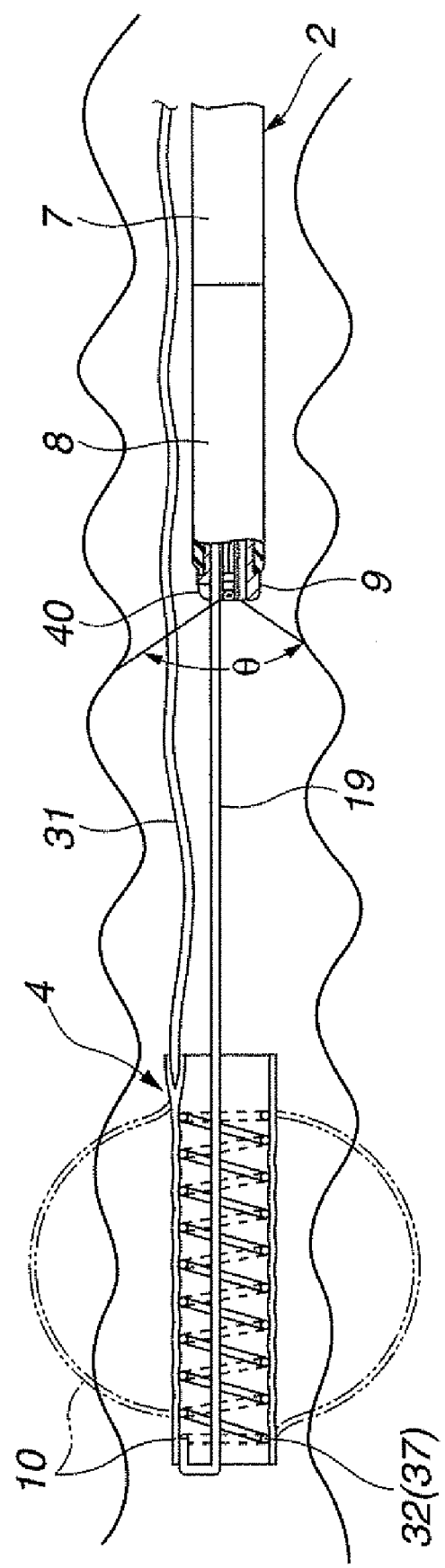
FIG. 4 is a diagram showing a state in which a balloon of the endoscope insertion support tool is moved forward from a state in FIG. 3.

First, as shown in FIG. 4, the operator pushes out the shaft 19 and moves the balloon 10 to the front side of the visual field from distal end portion 9 and the bending portion 8. θ shown in FIG. 4 indicates the visual field range of the observation window 11. When the shaft 19 is pushed out and the balloon peripheral portion is moved to the front side of the distal end portion 9 as shown in FIG. 4, the balloon peripheral portion enters the visual field range θ. The operator can perform operation for insertion while observing the balloon peripheral portion.

Next, the operator supplies the air 42 into the balloon 10 via the fluid tube 31, inflates the balloon 10 as indicated by an alternate long and two short dashes line in FIG. 4, and holds (fixes) the balloon peripheral portion in the intestinal tract with the inflated balloon 10.

Figure 5:
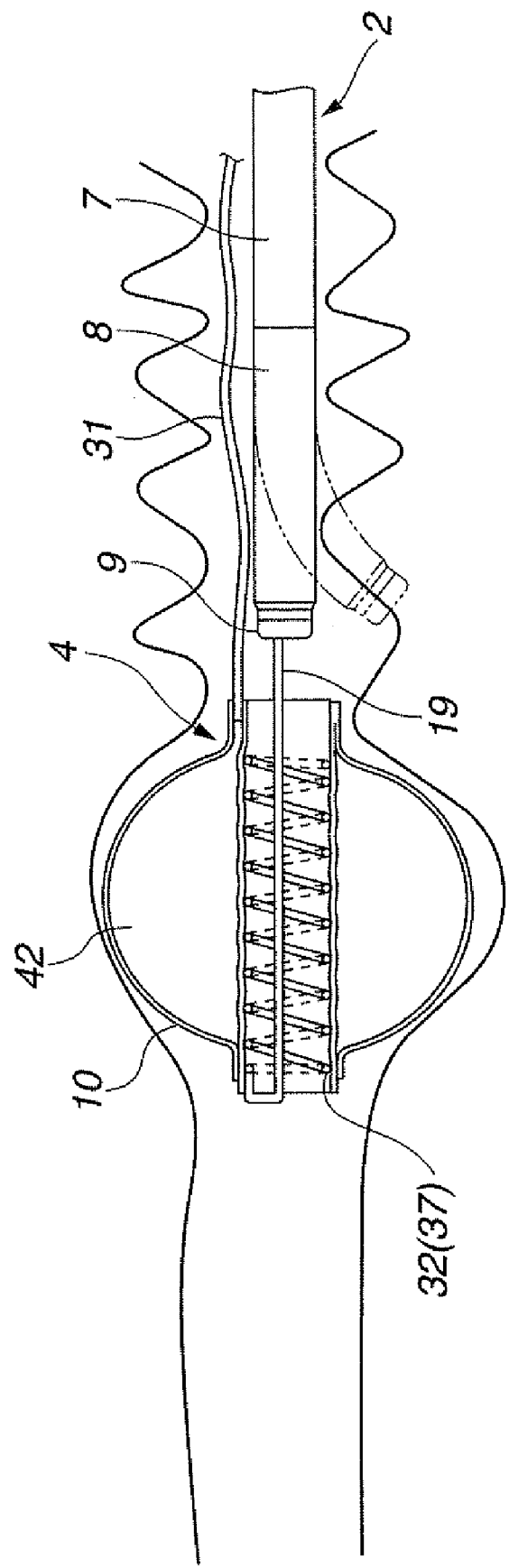
FIG. 5 is a diagram showing a state in which, after the balloon is inflated in the state in FIG. 4, operation for pulling in a shaft is performed to draw in an intestinal tract.

Next, as shown in FIG. 5, the operator performs operation for slowly pulling in the shaft 19 and draws in the intestinal tract with the balloon 10 inflated by the air 42. In this case, since the inflated balloon 10 is held in the intestinal tract by the inflation, the operator can move the distal end portion 9 on the rear side of the balloon 10 (which is more easily moved than the held balloon 10) to the balloon 10 side by performing the operation for pulling in the shaft 19.

Consequently, it is possible to advance the endoscope 2 to the balloon 10 side. Further, since it is possible to form the balloon 10 in a relatively large size, it is possible to increase the holding force of the balloon 10 and surely advance the endoscope 2.

Next, the operator slightly bends the bending portion 8 of the endoscope 2 as indicated by an alternate long and two short dashes line and presses the intestinal tract drawn in by the balloon 10 with the bending portion 8 to prevent the intestinal tract from returning to an original state thereof.

In that state, the operator deflates the balloon 10 and performs operation of the shaft 19 to push out the balloon 10 to the front side of the visual field again. A state in which the balloon 10 is deflated and pushed out to the front of the visual field again in this way is shown in FIG. 6.

Figure 6:
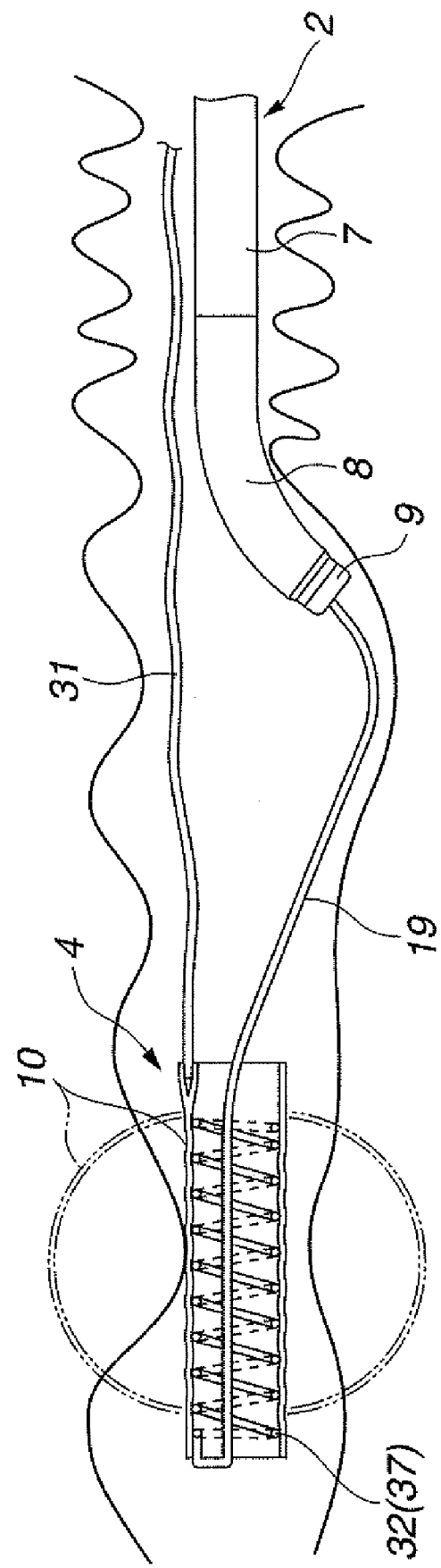
FIG. 6 is a diagram showing a state in which, after a bending portion is bent and the balloon is deflated in the state in FIG. 5, the balloon is moved forward.

The operator further inflates the balloon 10 from the state in FIG. 6 and releases the bend of the bending portion 8 to bring the balloon 10 into a state for drawing in the intestinal tract again. This state is shown in FIG. 7.

Figure 7:
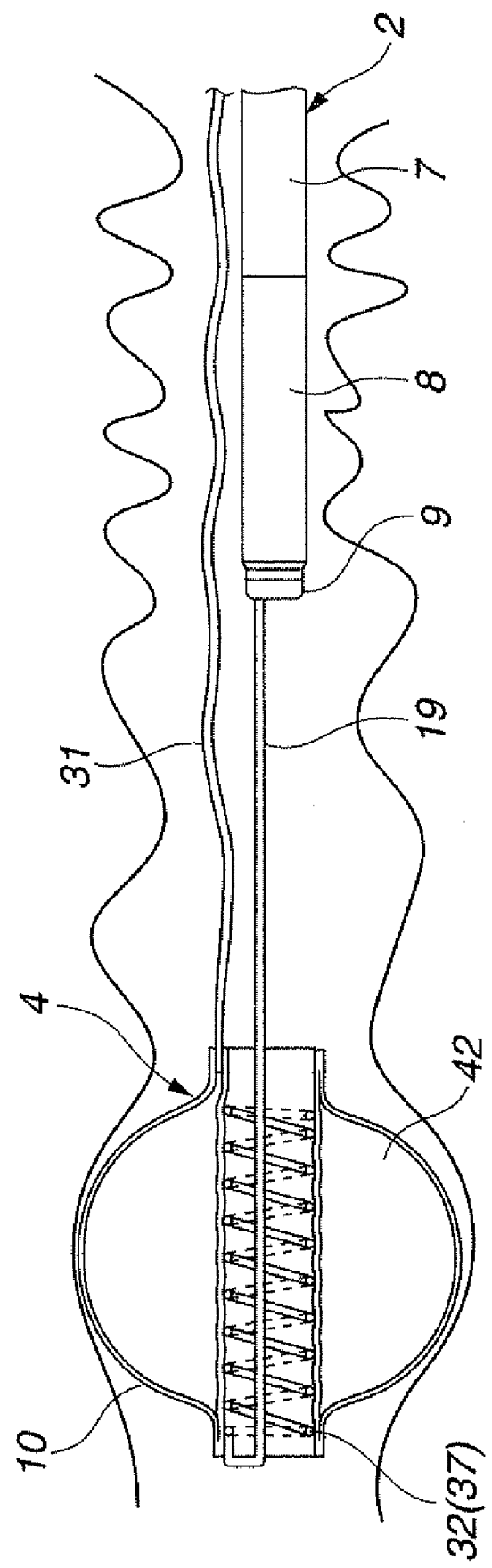
FIG. 7 is a diagram showing a state in which the balloon is inflated in the state in FIG. 6.

In a state of the balloon 10 inflated by the air 42 as shown in FIG. 7, the operator performs the operation for slowly pulling in the shaft 19 and draws in the intestinal tract with the balloon 10 in the inflated state. The operator draws in the intestinal tract with the balloon 10 inflated as shown in FIG. 8 and advances the endoscope 2.

By repeating such operation, the operator can relatively advance a distal end position of the endoscope 2 to the depth side of the intestinal tract in a short time.

Occasionally, in a state in which the distal end side of the endoscope 2 is inserted to a depth side of a spleen bend in the large intestine as shown in FIG. 9A, the operator inflates the balloon 10, brings the balloon 10 into a state in which the balloon 10 is fixed in the intestinal tract, and performs operation for slowly drawing out both the endoscope 2 and the shaft 19 of the endoscope insertion support tool 4 to the side close to the operator together. In this way, the operator can also straighten an intestinal tract portion of a colon sigmoideum portion or the like as shown in FIG. 9B.

By positively straightening the intestinal tract in this way, a force is easily transmitted to the distal end of the endoscope 2 and, moreover, the shaft 19 functions as an insertion guide for the endoscope 2. Therefore, it is possible to advance the distal end of the endoscope 2 to the depth of the intestinal tract not only by the draw-in of the intestinal tract but also by the advance of the endoscope 2.

The operator combines the draw-in of the intestinal tract and the straightening of the intestinal tract and repeats these kinds of operation several times to finally insert the endoscope 2 to a deepest portion of the intestinal tract.

Figure 10:
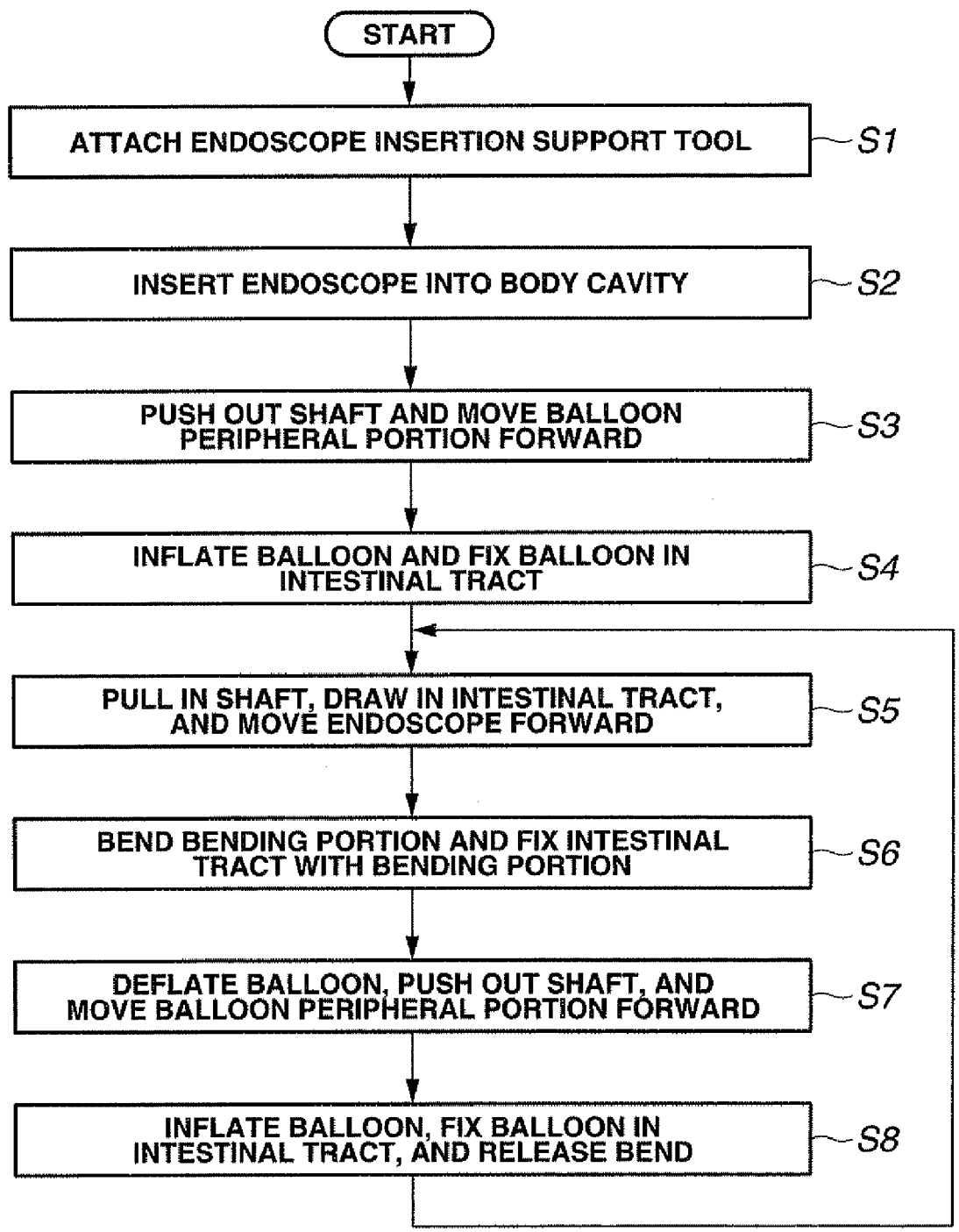
FIG. 10 is a flowchart of actions according to the present embodiment.

An overview of a method of supporting insertion of the insertion section 3 shown in FIGS. 3 to 8 is indicated by a flowchart as shown in FIG. 10.

In first step S1, the operator attaches the endoscope insertion support tool 4 near the distal end portion 9 of the insertion section 3 of the endoscope 2.

As shown in step S2, the operator inserts the insertion section 3 of the endoscope 2 into a body cavity, for example, into the intestinal tract of the large intestine from the anus starting from the distal end portion 9 side thereof.

When it is not easy to insert the insertion section 3 in the operation for pushing in the insertion section 3, as shown in step S3, the operator pushes out the shaft 19 and moves the balloon peripheral portion to the front side of the visual field from the distal end portion 9 and the bending portion 8 as shown in FIG. 4.

In the next step S4, the operator supplies the air 42 into the balloon 10 via the fluid tube 31, inflates the balloon 10, and holds and fixes the balloon 10 in the intestinal tract as indicated by the alternate long and two short dashes line in FIG. 4.

In the next step S5, as shown in FIG. 5, the operator performs the operation for slowly pulling in the shaft 19 and draws in the intestinal tract with the balloon 10 inflated by the air 42. The operator moves the endoscope 2 to the balloon 10 side, i.e., forward.

In the next step S6, the operator slightly bends the bending portion 8 of the endoscope 2 as indicated by the alternate long and two short dashes line in FIG. 5 and presses and fixes the intestinal tract drawn in by the balloon 10 with the bending portion 8 to prevent the intestinal tract from returning to the original state.

In that state, the operator deflates the balloon 10 as shown in step 87, pushes out the balloon 10 to the front of the visual field again, and brings the balloon 10 into the state shown in FIG. 6.

As shown in step S8, from the state in FIG. 6, the operator inflates the balloon 10, fixes the balloon 10 in the intestinal tract, and releases the bend of the bending portion 8.

Thereafter, returning to step S5, the operator performs the operation for pulling in the shaft 19, and draws in the intestinal tract again to move the endoscope 2 forward.

In this way, the operator can smoothly insert the endoscope 2 to the depth side of the intestinal tract.

According to the present embodiment, since the shaft 19 of the endoscope insertion support tool 4 is thin, a frictional force between the shaft 19 and the second channel 18 is extremely small. It is possible to perform operation for advancing and retracting the endoscope insertion support tool 4 with a light force at a level of insertion of the treatment instrument.

Moreover, since a curvature radius of the shaft 19 itself is also small, it is easy to pass the shaft 19 through a bending portion having a small curvature radius in the body cavity.

When the balloon 10 is inflated and fixed in the intestinal tract, since the balloon 10 can always be checked in the visual field, the balloon 10 can be easily fixed and, therefore, an inspection time can be reduced.

By completely pulling in the shaft 19 or completely pushing in the endoscope 2 with the shaft 19 as a guide, it is possible to move the balloon 10 and the balloon holding member 32 from the inside to the outside of the visual field. Therefore, it is possible to efficiently perform observation or treatment with a wide visual field.

Since the balloon holding member 32 and the shaft 19 are made of the flexible member as described above, even in a state in which the balloon 10 is housed on the bending portion 8, it is possible to perform the operation for bending the endoscope 2 without any trouble.

Since the balloon 10 can be attached near the outer peripheral surfaces of the distal end portion 9 and the bending portion 8, it is possible to adopt a large balloon having a large fixing force for fixing to the intestinal tract compared with a balloon like a balloon catheter that is inserted into a treatment instrument insertion channel from a side close to the operator. The operator can mount the large balloon 10 having the large fixing force on the outer peripheral surfaces of the distal end portion 9 and the bending portion 8. As a method of mounting the balloon 10, since the operator has only to insert the shaft 19 starting from the distal end side thereof, the method can be simplified.

Even in a state in which the balloon 10 is pushed forward and sufficiently placed in the visual field, the operation for bending the endoscope 2 is possible. Thus, it is also easy to delicately control a position of the balloon 10 with the bending operation and insert the balloon 10 further to the depth.

It is also possible to easily perform operation for pushing, pulling, and twisting the endoscope 2.

In the attached state shown in FIG. 1, a part of the endoscope insertion support tool 4 is fit in the recess 40 provided at the distal end portion 9 of the endoscope 2 and the endoscope insertion support tool 4 is positioned in a rotating direction (a peripheral direction). Therefore, even in the twisting operation during insertion of the endoscope 2, the endoscope insertion support tool 4 does not wobble and can be inserted integrally with the endoscope 2.

Note that, as a modification of the first embodiment, the shaft 19 as a moving member may be inserted through the fluid tube 31.

Instead of attaching the balloon 10 to the outer peripheral surfaces of the distal end portion 9 and the bending portion 8, the shaft 19 may be increased in length and attached to the outer peripheral surface of the flexible tube portion 7. In that cases since nothing is attached to the bending portion 8, the operator can perform, in a sense same as that in operating a normal endoscope, the bending operation with light operation as if no load is applied.

Moreover, the balloon 10 may be attached from the distal end portion 9 to the bending portion 8 or from the bending portion 8 to the flexible tube portion 7 in such a manner as to extend over the respective portions. Since the balloon 10 extends over the respective portions, it is unnecessary to form the balloon 10 in length fit in the respective portions and it is possible to give a degree of freedom to the length in the axial direction of the balloon 10.

Second Embodiment

Figure 11:
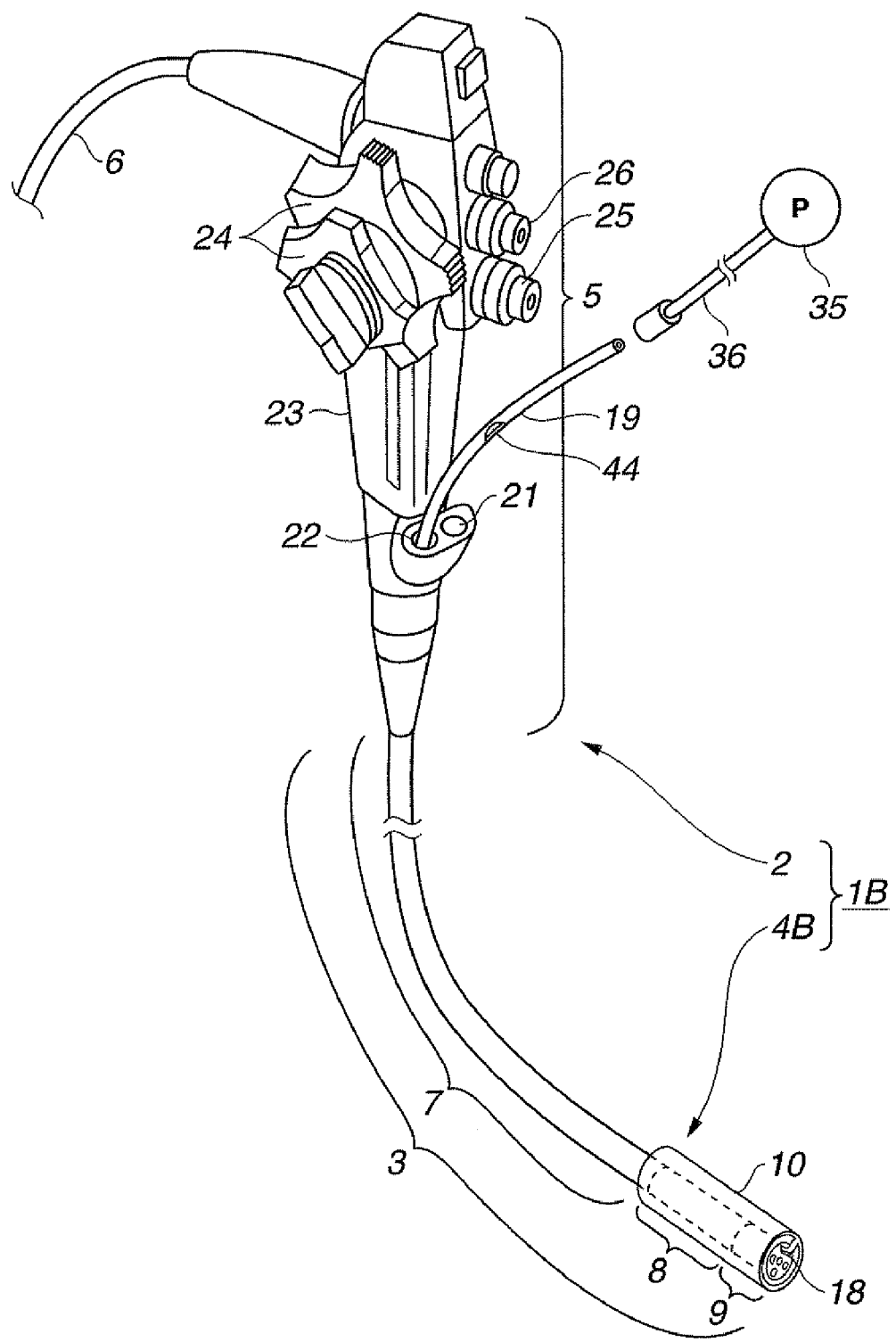
FIG. 11 is a perspective view showing an overall configuration of an endoscope device according to a second embodiment of the present invention.

A second embodiment of the present invention is explained with reference to FIGS. 11 and 12. FIG. 11 shows an endoscope device 1B including the second embodiment of the present invention.

The endoscope device 1B includes the endoscope 2 same as that in the case of the first embodiment and an endoscope insertion support tool 4B according to the second embodiment.

In the endoscope insertion support tool 4B according to the present embodiment, the fluid tube 31 shown in FIG. 1 is not provided and, instead, a fluid supplying conduit 44 is formed in the shaft 19. In other words, the shaft 19 is configured by a hollow body. The rear end of the shaft 19 pulled out from the second channel insertion port 22 to the outside is hermetically connected to a connecting portion at a rear end of the tube 36 connected to the balloon control pump 35.

The operator can freely inflate and deflate the balloon 10 by turning on and off a not-shown balloon control switch.

Since the fluid tube 31 is not provided, the medical tape 33 that fixes the fluid tube 31 is also unnecessary.

Figure 12:
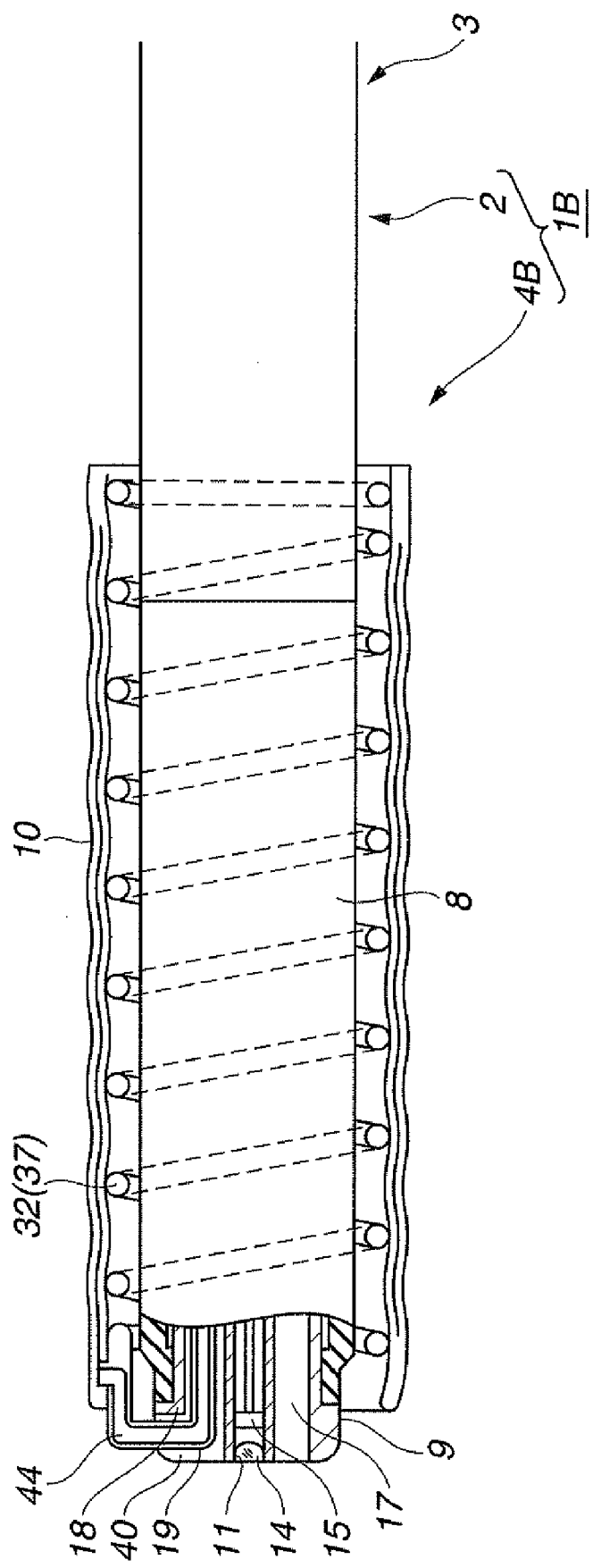
FIG. 12 is a sectional view showing a distal end side of an insertion section of an endoscope attached with an endoscope insertion support tool.

FIG. 12 shows a configuration on the distal end side of the insertion section 3 of the endoscope 2 attached with the endoscope insertion support tool 4B. As described above, in the endoscope insertion support tool 4B, the shaft 19 in the endoscope insertion support tool 4 in FIG. 3 is formed of a hollow tubular member and the fluid supplying conduit 44 is formed in a hollow portion of the shaft 19.

A distal end of the fluid supplying conduit 44 communicates with an opening of the balloon 10 and a part of the fluid supplying conduit 44 is formed thick and integrated with the spring 37 configuring the balloon holding member 32.

The other components are the same as those shown in FIGS. 1 to 3. Actions of the present embodiment are substantially the same as those in the first embodiment shown in FIGS. 1 to 10.

As effects of the present embodiment, besides all the effects explained in the first embodiment, since the fluid tube 31 is not provided on the outside of the endoscope 2, it is possible to more easily insert the endoscope 2 than in the case of the first embodiment.

Figure 13:
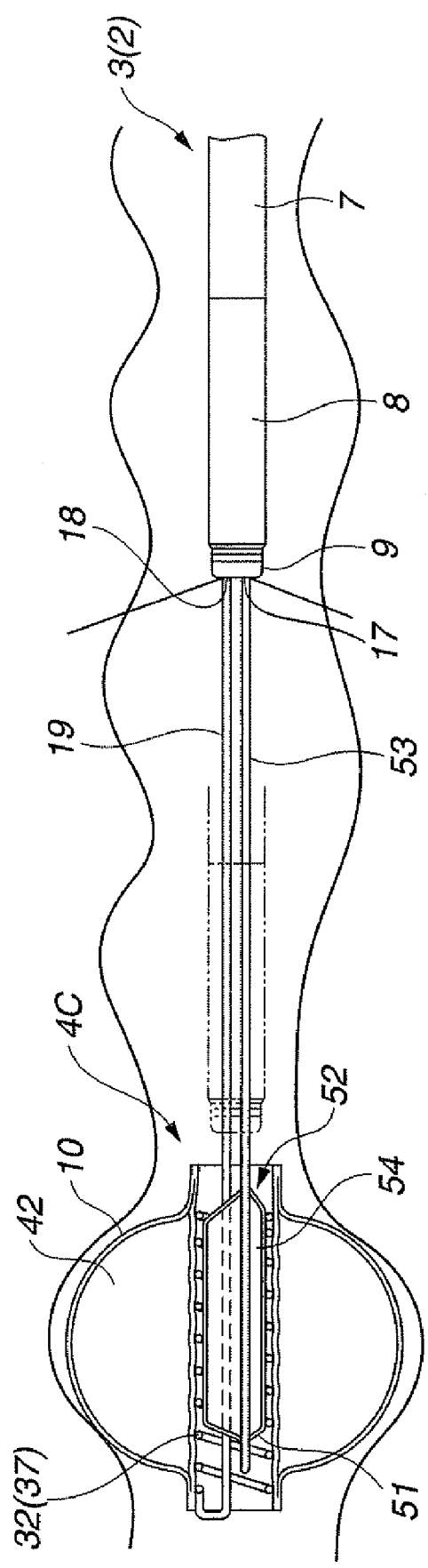
FIG. 13 is a diagram showing an endoscope insertion support tool according to a modification in a state of use.

A modification in the present embodiment is shown in FIG. 13 in a state of use thereof. In an endoscope insertion support tool 4C according to the present modification shown in FIG. 13, a catheter portion (a hollow shaft portion) 53 of a balloon catheter 52 attached with a balloon 51 at a distal end thereof is inserted through the first channel 17 from a side close to the operator in the endoscope insertion support tool 4B according to the second embodiment shown in FIGS. 11 and 12. The balloon 51 at the distal end is inflated by a fluid such as the air 54, the inflated balloon 51 is fixed in the inside of the balloon holding member 32.

In this state, the shaft 19 is also fixed by (close adhesion with) the balloon 51 inflated in the balloon holding member 32.

With both the shaft 19 and (the catheter portion 53 of) the balloon catheter 52 fixed in the balloon holding member 32 in this way as guides, it is possible to prevent the endoscope 2 from rotating as indicated by an alternate long and two short dashes line in FIG. 13 and, for example, move the endoscope 2 forward.

Therefore, the present modification has an advantage that it is possible to more smoothly perform insertion work. Otherwise, the present modification has effects same as those in the second embodiment.

In the present modification, the example in which the balloon catheter 52 is applied to the endoscope insertion support tool 4B according to the second embodiment is explained. However, the balloon catheter 52 can be applied in the same manner in the case of the first embodiment.

Third Embodiment

Figure 14:
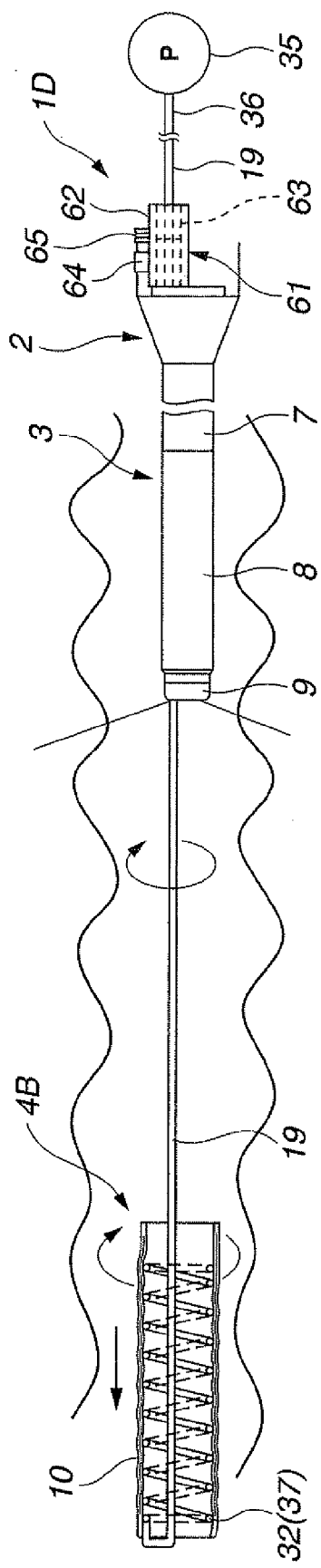
FIG. 14 is a diagram showing a schematic configuration of an endoscope device according to a third embodiment of the present invention.

A third embodiment of the present invention is explained with reference to FIG. 14. FIG. 14 shows an endoscope device 1D including the third embodiment of the present invention in a state of use thereof.

In the endoscope device 1D, the shaft 19 further pulled out from the second channel insertion port 22 to the outside in the endoscope 1B according to the second embodiment is attached to, for example, the second channel insertion port 22, inserted through a rotating device 61 that rotates the shaft 19, and, then, connected to the balloon control pump 35 shown in FIG. 11 via the connecting portion. In FIG. 14, a balloon peripheral portion side is denoted by reference sign 4B because the balloon peripheral portion side has a configuration same as that of, for example, the second embodiment.

The rotating device 61 is extended to the outside, for example, in a state in which the shaft 19 is attached to a hollow portion of a motor 63 provided in a cylinder 62 grasped by the operator. By turning on a switch 64 provided in the cylinder 62, the motor 63 rotates and the shaft 19 can be rotated by the rotation of the motor 63.

Besides the switch 64, a button 65 for adjusting rotating speed of the motor 63 is also provided. The operator can freely set rotating speed of the shaft 19.

In the present embodiment, besides the functions in the second embodiment, the shaft 19 is rotated to make it possible to rotate the balloon 10 side at the distal end thereof as well.

When the balloon 10 side is rotated, since a frictional resistance with the intestinal tract can be reduced, it is possible to more easily push the balloon 10 side into the depth side than the case in which the balloon 10 is not rotated. Other actions and effects are the same as those in the second embodiment.

Fourth Embodiment

Figure 15:
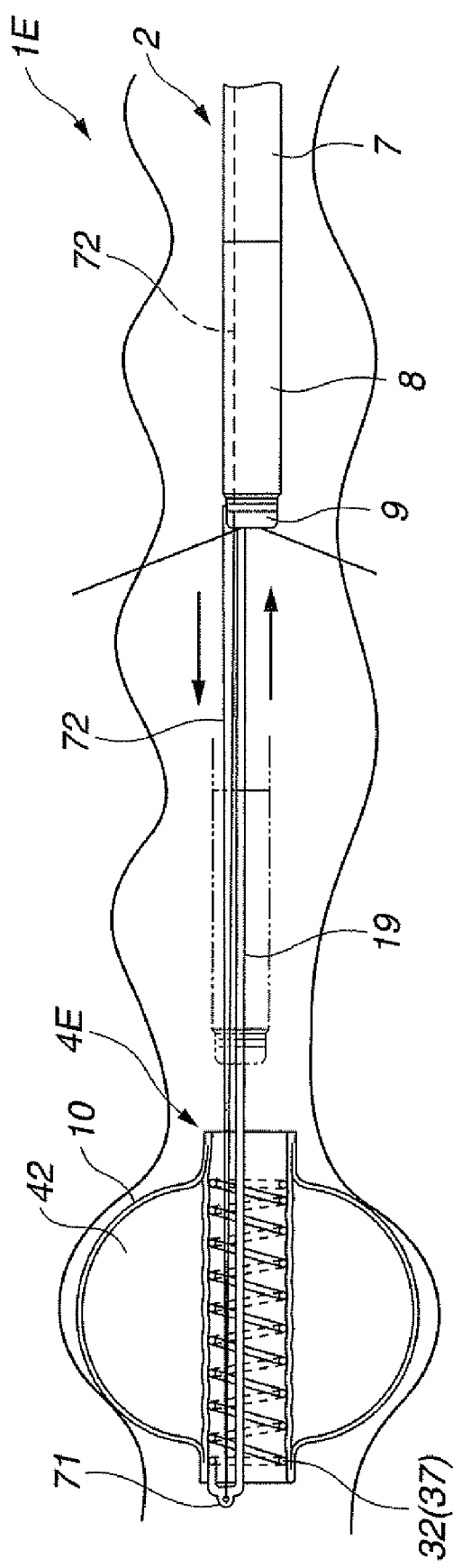
FIG. 15 is a diagram showing a schematic configuration of an endoscope device according to a fourth embodiment of the present invention.

A fourth embodiment of the present invention is explained with reference to FIG. 15. FIG. 15 shows a distal end side of an endoscope device 1E including the fourth embodiment of the present invention.

The endoscope device 1E includes the endoscope 2 and an endoscope insertion support tool 4E.

In the endoscope insertion support tool 4E according to the present embodiment, for example, a hole portion 71 is provided in the return portion at the distal end of the shaft 19 as shown in FIG. 15 in, for example, the endoscope insertion support tool 4B according to the second embodiment. For example, a string 72 is inserted through the hole portion 71. One end (a distal end) of the string 72 is fixed to the distal end portion 9 of the endoscope 2 by binding or the like. The other end (a rear end) of the string 72 is inserted through the second channel 18 in the same manner as the shaft 19 and extended to the outside from the second channel insertion port 22 not shown in the figure such that the string 72 can be pulled by the operator.

When the endoscope insertion support tool 4E is used for insertion support, in a state in which the balloon 10 is inflated and fixed in the intestinal tract as shown in FIG. 15, the operator can move the distal end side of the insertion section 3 of the endoscope 2 to the front side of the visual field as indicated by an alternate long and two short dashes line in FIG. 15 by pulling the string 72 to the side close to the operator. Other components and actions are the same as those in the second embodiment.

The present embodiment has effects substantially the same as those in the second embodiment.

Figure 16:
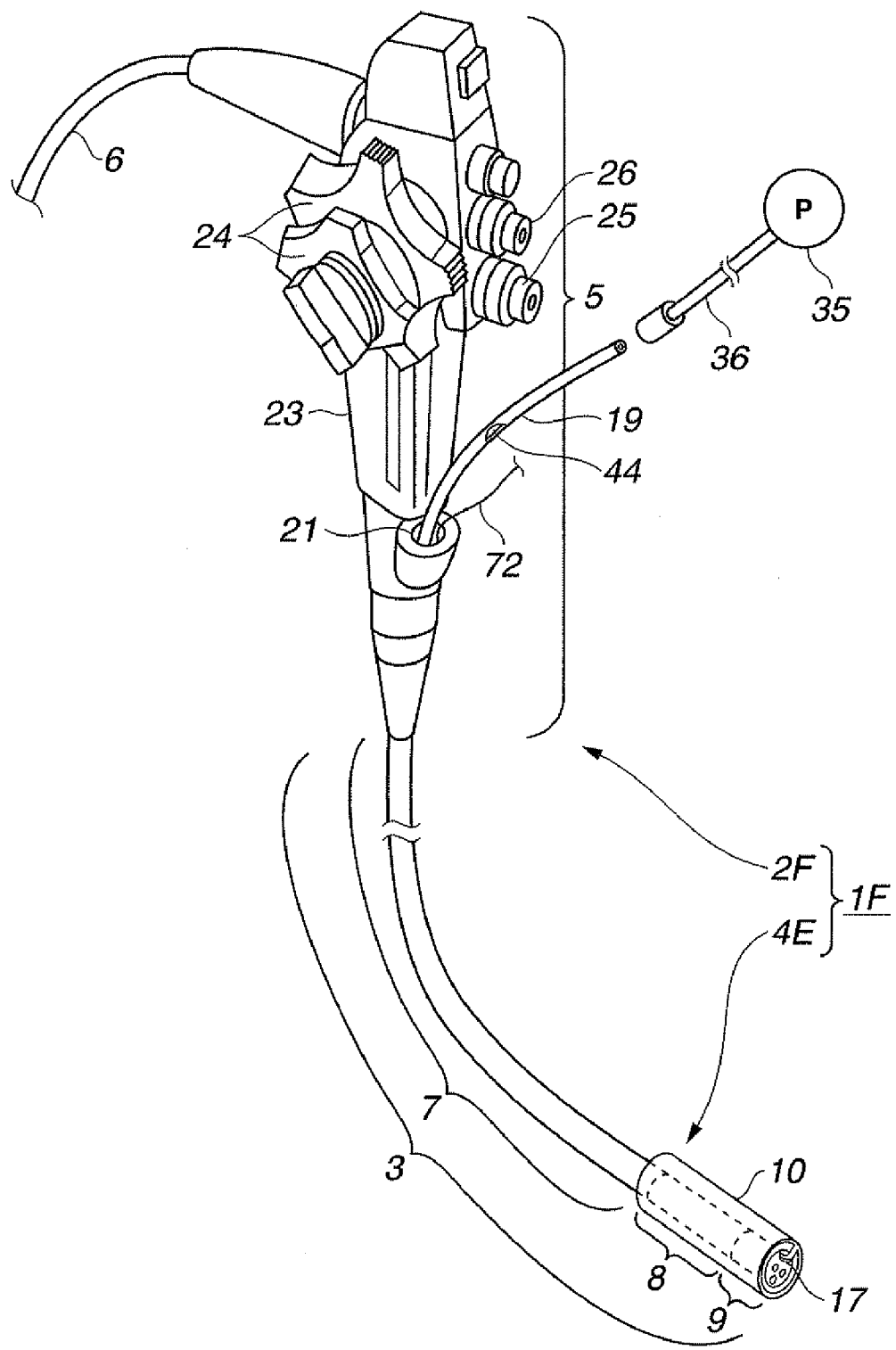
FIG. 16 is a perspective view showing an overall configuration of an endoscope device according to a modification.

FIG. 16 shows an endoscope device 1F including an endoscope 2F according to a modification of the fourth embodiment.

In the endoscope device 1F, the second channel 18 is not provided in the endoscope 2 in the fourth embodiment (or the first embodiment) and the endoscope 2F includes only the first channel 17.

The shaft 19 and the string 72 in the endoscope insertion support tool 4E are inserted through the first channel 17 and extended to the outside from the first channel insertion port 21.

In the endoscope 2F, the function of suction is secured in a clearance portion between the shaft 19 (and the string 72) and the first channel 17. When the treatment instrument is used, a distal end side of the treatment instrument is passed through the clearance portion and projected to the body cavity side from the distal end opening.

According to the endoscope 2F in the present modification, since a conduit (a channel) exclusive for operating the endoscope insertion support tool 4E is unnecessary, it is possible to use a normal endoscope. In other words, the normal endoscope can also be smoothly and easily inserted into the large intestine and the like according to the present modification. It is possible to expand an application range of the insertion of the endoscope.

In the endoscope 2F according to the present modification, suction performance (ability) and treatment performance (ability) are a little lower than those in the case of the endoscope 2 according to the first embodiment. However, since an external shape of the insertion section 3 can be reduced in diameter, an application range in which the insertion section 3 can be inserted is broadened.

Otherwise, the present modification has effects same as those in the fourth embodiment. It is also possible to apply the endoscope 2F according to the present modification to the embodiments other than the fourth embodiment.

The endoscope insertion support tool 4E may be the endoscope insertion support tool 4 according to the first embodiment and the endoscope insertion support tool 4B according to the second embodiment.

Fifth Embodiment

Figure 17:
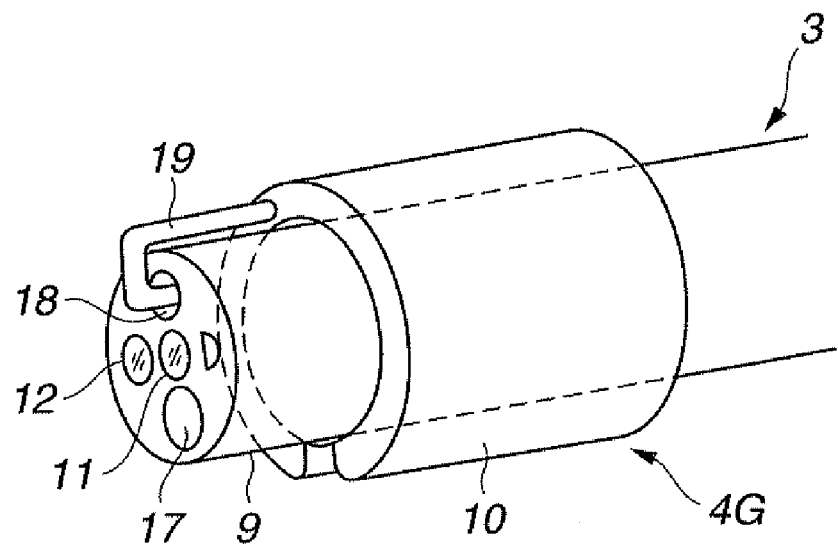
FIG. 17 is a diagram showing an endoscope insertion support tool according to a fifth embodiment of the present invention.

A fifth embodiment of the present invention is explained with reference to FIG. 17. FIG. 17 shows a shape of the peripheral portion of the balloon 10 in an endoscope insertion support tool 4G according to the fifth embodiment of the present invention. In the first embodiment, the second embodiment, and the like, the balloon 10 is formed in the shape that covers the outer peripheral surface near the distal end portion 9 in a cylindrical shape. However, in the present embodiment, a cross section thereof is formed in a C ring shape.

Besides the balloon 10, the balloon holding member 32 that holds the balloon 10 may also be formed in a C ring shape. Other components are the same as those in, for example, the second embodiment. Actions and effects in the fifth embodiment are substantially the same as those in the second embodiment. The fifth embodiment can also be applied to the embodiments other than the second embodiment.

Figure 18:
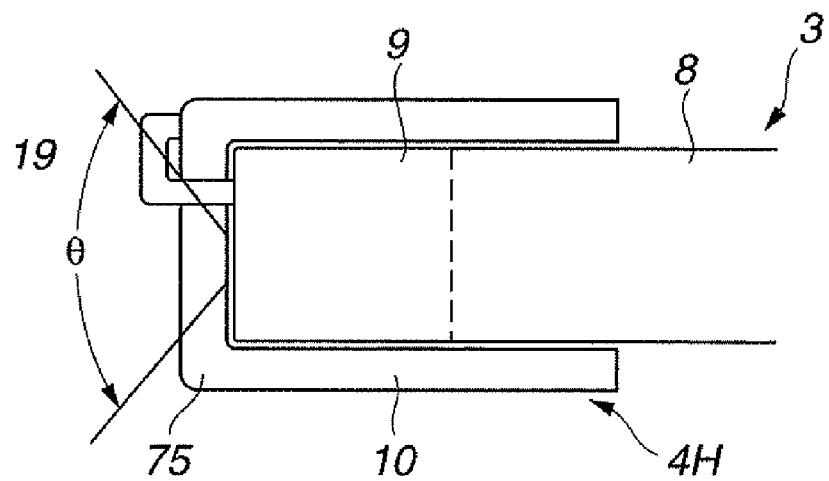
FIG. 18 is a diagram showing an endoscope insertion support tool according to a modification.

FIG. 18 shows a shape of the peripheral portion of the balloon 10 in an endoscope insertion support tool 4H according to a modification. In the endoscope insertion support tool 4H, in the balloon 10 of a cylindrical shape in the first embodiment the second embodiment and the like, a balloon section 75 is also provided on the distal end surface side thereof to form a balloon of a cap shape.

In this case, the balloon section 75 is formed of, at least a transparent body to secure a function of transmitting illumination light and observation light. It goes without saying that other balloon sections may be formed of transparent bodies.

Only the balloon section 75 may be increased in thickness such that the balloon section 75 is hardly deformed by the supply and discharge of a fluid. The balloon holding member 32 may be formed in a spiral shape as in the first embodiment the second embodiment, and the like or may be formed in a cap shape in the same manner as the balloon 10 formed in the cap shape.

Other components are the same as those in, for example, the second embodiment. Actions and effects in the modification are substantially the same as those in the second embodiment. The modification can also be applied to the embodiments other than the second embodiment.

Sixth Embodiment

Figure 19:
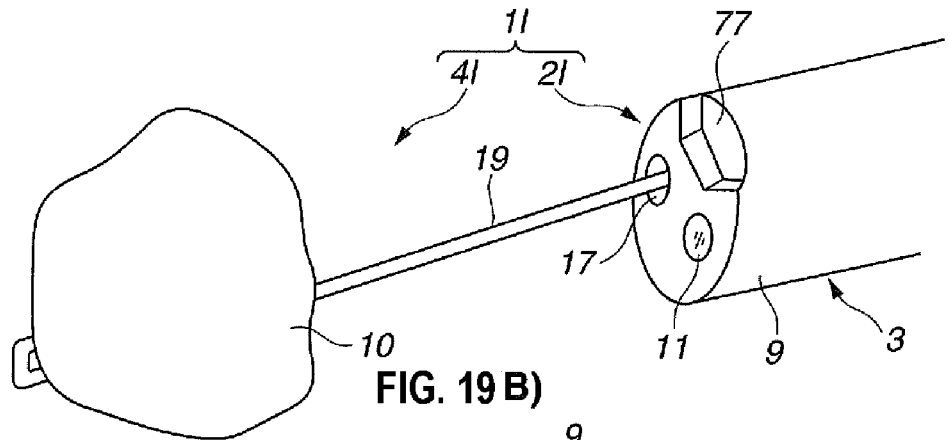
FIGS. 19A and 19B are diagrams showing a schematic configuration of an endoscope device according to a sixth embodiment of the present invention.
Figure 19:
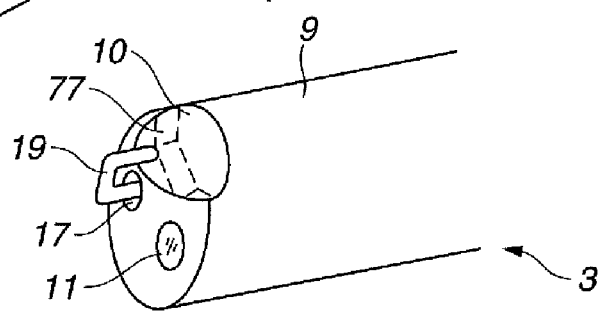

A sixth embodiment of the present invention is explained with reference to FIGS. 19A and 19B. FIGS. 19A and 19B show a configuration of a distal end side of an endoscope device 1I according to the sixth embodiment of the present invention. The endoscope device 1I includes an endoscope insertion support tool 4I and an endoscope 2I. In the endoscope insertion support tool 4I, the balloon holding member 32 is not provided and the balloon 10 is attached to the distal end of the shaft 19. In FIG. 19A, a state in which the balloon 10 is inflated is shown. The inflated balloon 10 may be formed in a spherical shape.

The balloon 10 is deformed to be sufficiently small when the balloon 10 is deflated.

A recess is provided and a balloon attaching portion 77 is provided on the distal end surface of the distal end portion 9 of the endoscope 2I. The balloon 10 deflated by the balloon attaching portion 77 can be stored in the balloon attaching portion 77 as shown in FIG. 19B. The present embodiment also has actions and effects similar to those in the first embodiment and the like.

Figure 20:
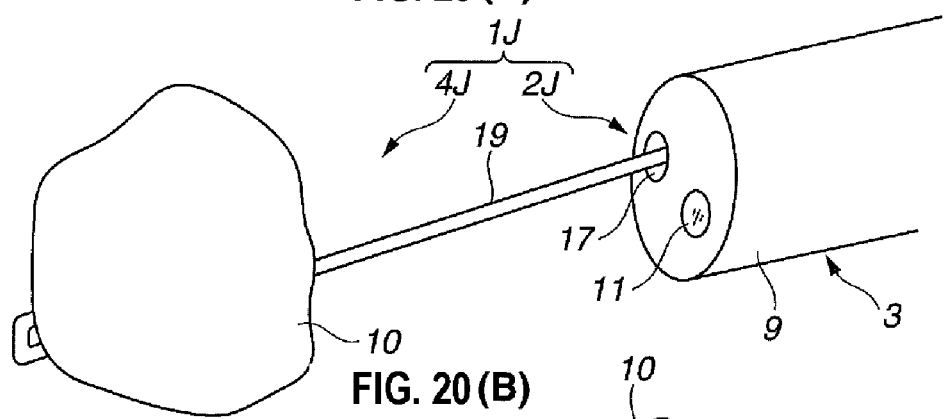
FIGS. 20A and 20B are diagrams showing a schematic configuration of an endoscope device according to a modification.
Figure 20:
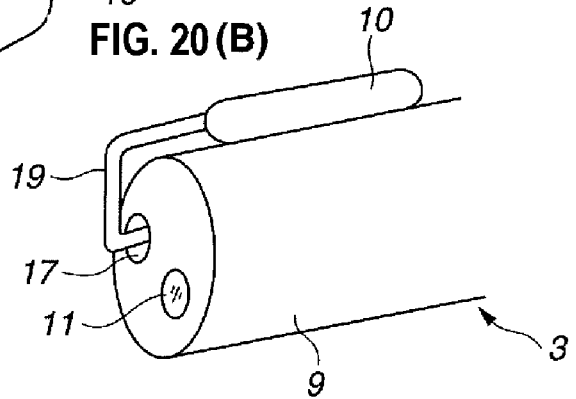

FIGS. 20A and 20B show a configuration of a distal end side of an endoscope device 1J according to a modification of the sixth embodiment. The endoscope device 1J includes the endoscope insertion support tool 4I and an endoscope 2J. In the endoscope 2J, the balloon attaching portion 77 formed by the recess is not provided in the endoscope 2I in FIGS. 19A and 19B. An attaching portion is formed on the outer peripheral surface of the distal end portion 9 of the endoscope 2J.

By deflating the balloon 10 inflated as shown in FIG. 20A, the deflated balloon 10 can be attached near the outer peripheral surface of the distal end portion 9 of the endoscope 2J as shown in FIG. 20B. Other components and effects are the same as those in the sixth embodiment in FIGS. 19A and 19B.

For example, in the first embodiment in FIG. 1, the rear end side of the shaft 19 configuring the advancing and retracting member may be attached to a not-shown rotational operation member in the inside of the operation section 23 of the endoscope 2. The shaft 19 may be advanced and retracted by operation of the operator for rotating the rotational operation member.

Embodiments configured by, for example, partially combining the embodiments described above also belong to the present invention.

INDUSTRIAL APPLICABILITY

In a balloon detachably attached to near a distal end portion of an insertion section, a balloon peripheral portion is moved from the distal end portion of the insertion section to a front side of a visual field by pushing out an advancing and retracting member, the balloon is inflated by a fluid and fixed in a tube cavity such as an intestinal tract, and, then, operation for pulling in the advancing and retracting member to a side close to an operator to make it possible to surely move an endoscope to the balloon side. This makes it possible to smoothly and easily insert the endoscope to a depth side in the tube cavity and perform an endoscope inspection smoothly and in a short time.

This application is filed claiming priority of Japanese Patent Application No. 2005-288213 filed in Japan on Sep. 30, 2005. The disclosed contents are cited in the specification of this application, claims, and the drawings.

The invention claimed is:

1. An endoscope insertion support tool comprising:
an advancing and retracting member that is inserted through a channel disposed in an insertion section of an endoscope to be capable of advancing and retracting in the channel, a distal end side of the advancing and retracting member being capable of projecting from a distal end opening of the channel;
a balloon member that includes an attaching portion capable of attaching a cylindrical inner peripheral surface of the balloon member to an outer peripheral surface of the insertion section on a distal end side thereof including at least a distal end portion, over a substantially whole length of the balloon member when the advancing and retracting member is maximally retracted, the balloon member being connected to the distal end of the advancing and retracting member and capable of projecting from the distal end of the insertion section according to an advancing movement of the advancing and retracting member; and
fluid supplying and discharging means including a conduit that is connected to the balloon member and inflates and deflates the balloon member according to supply and discharge of a fluid to and from the balloon member with a diameter of the cylindrical inner peripheral surface of the balloon member maintained.

2. The endoscope insertion support tool according to claim 1, wherein the balloon member is formed in a hollow shape in a central axis side portion in the cylindrical shape and has the inner peripheral surface that forms an attaching portion attachable to the outer peripheral surface of the insertion section on the distal end side thereof.

3. The endoscope insertion support tool according to claim 1, wherein the balloon member is formed in a C shape in a section in a radial direction having the inner peripheral surface as the attaching portion.

4. The endoscope insertion support tool according to claim 1, wherein the advancing and retracting member is a shaft body insertable through the channel.

5. The endoscope insertion support tool according to claim 4, wherein the shaft body includes the conduit in the inside thereof and is a hollow body insertable through the channel.

6. The endoscope insertion support tool according to claim 4, further including driving means for causing the shaft body to perform at least one operation of advancing and retraction and rotation with respect to the insertion section.

7. The endoscope insertion support tool according to claim 4, further comprising fixing means for detachably fixing the balloon member or the shaft body to the insertion section.

8. The endoscope insertion support tool according to claim 1, further comprising:
a balloon that is inflated by supply of the fluid; and
a balloon holding member that holds the balloon and includes the attaching portion that is detachably attached to the outer peripheral surface on the distal end side of the insertion portion.

9. The endoscope insertion support tool according to claim 8, wherein an inner peripheral surface of the balloon holding member is formed in a shape that fits on the outer peripheral surface of the distal end side of the insertion section.

10. The endoscope insertion support tool according to claim 1, wherein the attaching portion makes the whole of the cylindrical inner peripheral surface of the balloon member be capable of being attached to the outer peripheral surface of the distal end portion of the insertion section and a bending portion which is provided at a proximal end of the distal end portion when the balloon member is either in an inflated state or in a deflated state.

11. The endoscope insertion support tool according to claim 1, wherein when the balloon member is attached to the outer peripheral surface of the insertion portion on the distal end side thereof by the attaching portion, a distal end surface of the balloon member is capable of being arranged at a more proximal position than a position of the distal end surface of the insertion section.

12. The endoscope insertion support tool according to claim 1, wherein the attaching portion has openings at both ends of the cylindrical inner peripheral surface.

13. The endoscope insertion support tool according to claim 1, wherein the advancing and retracting member is capable of projecting forward by 50 cm or more from the distal end surface of the endoscope.

14. An endoscope device comprising:
an endoscope including a slim insertion section that is insertable into a body cavity and is provided with an illumination window and an observation window at a distal end surface of at a distal end portion of the endoscope;
an advancing and retracting member that is inserted through a channel disposed in the insertion section to be capable of advancing and retracting in the channel, a distal end side of the advancing and retracting member being capable of projecting from a distal end opening of the channel;
a balloon member that includes an attaching portion capable of attaching a cylindrical inner peripheral surface of the balloon member to an outer peripheral surface of the insertion section on a distal end side thereof including at least a distal end portion, over a substantially whole length of the balloon member when the advancing and retracting member is maximally retracted, the balloon member being connected to the distal end of the advancing and retracting member and capable of projecting from the distal end of the insertion section according to an advancing movement of the advancing and retracting member; and
a conduit that is connected to the balloon member and inflates and deflates the balloon member according to supply and discharge of a fluid to and from the balloon member with a diameter of the cylindrical inner peripheral surface of the balloon member maintained.

15. The endoscope device according to claim 14, wherein the conduit is connected to fluid supplying and discharging means for supplying and discharging the fluid.

16. The endoscope device according to claim 14, wherein the balloon member is formed in a hollow shape in a central axis side portion in the cylindrical shape and has the inner peripheral surface that forms the attaching portion attachable to the outer peripheral surface of the insertion section on the distal end side thereof.

17. The endoscope device according to claim 14, wherein the balloon member is formed in a C shape in a section in a radial direction having the inner peripheral surface as the attaching portion.

18. The endoscope device according to claim 14, wherein the advancing and retracting member is a shaft body insertable through the channel.

19. The endoscope device according to claim 18, wherein the shaft body includes the conduit in the inside thereof and is a hollow body insertable through the channel.

20. The endoscope device according to claim 18, further including driving means for causing the shaft body to perform at least one operation of advancing and retraction and rotation with respect to the insertion section.

21. The endoscope device according to claim 18, further comprising fixing means for detachably fixing the balloon member or the shaft body to the insertion section.

22. The endoscope device according to claim 14, further comprising:
a balloon that is inflated by supply of the fluid; and
a balloon holding member that holds the balloon and includes the attaching portion that is detachably attached to the outer peripheral surface on the distal end side of the insertion portion.

23. The endoscope device according to claim 22, wherein an inner peripheral surface of the balloon holding member is formed in a shape that fits on the outer peripheral surface of the distal end side of the insertion section.

24. The endoscope device according to claim 14, wherein the balloon member is set to enter a visual field range of the observation window when the balloon member is projected from a distal end of the insertion section by the advancing and retracting member.

25. The endoscope device according to claim 14, wherein the balloon member is set in a visual field range of the observation window when the balloon member is projected from a distal end of the insertion section by the advancing and retracting member and is set outside the visual field range when the balloon member is attached to the insertion section.

26. The endoscope device according to claim 14, wherein the attaching portion makes the whole of the cylindrical inner peripheral surface of the balloon member be capable of being attached to the outer peripheral surface of the distal end portion of the insertion section and a bending portion which is provided at a proximal end of the distal end portion when the balloon member is either in an inflated state or in a deflated state.

27. The endoscope device according to claim 14, wherein when the balloon member is attached to the outer peripheral surface of the insertion portion on the distal end side thereof by the attaching portion, a distal end surface of the balloon member is capable of being arranged at a more proximal position than a position of the distal end surface of the insertion section.

28. The endoscope device according to claim 14, wherein the attaching portion has openings at both ends of the cylindrical inner peripheral surface.

29. The endoscope device according to claim 14, wherein the advancing and retracting member is capable of projecting forward by 50 cm or more from the distal end surface of the endoscope.

* * * * *